US009173967B1

(12) United States Patent
Biberger

(10) Patent No.: US 9,173,967 B1
(45) Date of Patent: *Nov. 3, 2015

(54) SYSTEM FOR AND METHOD OF PROCESSING SOFT TISSUE AND SKIN WITH FLUIDS USING TEMPERATURE AND PRESSURE CHANGES

(75) Inventor: Maximilian A. Biberger, Scottsdale, AZ (US)

(73) Assignee: SDCmaterials, Inc., Tempe, AZ (US)

( * ) Notice: Subject to any disclaimer, the term of this patent is extended or adjusted under 35 U.S.C. 154(b) by 1884 days.

This patent is subject to a terminal disclaimer.

(21) Appl. No.: 12/151,805

(22) Filed: May 8, 2008

Related U.S. Application Data

(60) Provisional application No. 60/928,946, filed on May 11, 2007.

(51) Int. Cl.

| *A61L 2/00* | (2006.01) |
| *B08B 5/00* | (2006.01) |
| *A61F 2/10* | (2006.01) |
| *A61L 2/18* | (2006.01) |
| *B22F 9/12* | (2006.01) |
| *B01J 19/00* | (2006.01) |
| *F28D 15/00* | (2006.01) |

(52) U.S. Cl.
CPC .............. *A61L 2/18* (2013.01); *B01J 19/0013* (2013.01); *B22F 9/12* (2013.01); *F28D 15/00* (2013.01); *B22F 2203/13* (2013.01)

(58) Field of Classification Search
CPC ... B22F 9/12; A61L 2430/40; A61L 27/3604; A61L 2/18; A61L 2/20; A61L 2/04; B01J 19/0013; F28D 15/00; F28D 7/024; C08J 2369/00; C08J 2433/08; C08J 2483/04; C08J 7/042; A61F 2/10; A61F 2/01; A61K 9/64; A61K 9/14
USPC .................. 424/423, 456, 28, 1, 292; 623/16, 623/15.11, 23.72, 920; 134/1, 2, 21, 31
See application file for complete search history.

(56) References Cited

U.S. PATENT DOCUMENTS

| 5,725,579 | A   |   | 3/1998  | Fages et al. ................ 623/16 |
| 6,149,864 | A   | * | 11/2000 | Dillow et al. ................ 422/28 |
| 7,008,591 | B2  | * | 3/2006  | Kafesjian et al. .............. 422/1 |
| 7,550,152 | B2  | * | 6/2009  | Pandit et al. ................ 424/423 |
| 8,007,718 | B1  |   | 8/2011  | Biberger |
| 8,012,414 | B2  | * | 9/2011  | Burns et al. ................ 422/33 |
| 8,388,944 | B2  | * | 3/2013  | Christensen ................ 424/93.1 |
| 8,945,219 | B1  |   | 2/2015  | Biberger |
| 2003/0027125 | A1 |   | 2/2003  | Mills et al. |
| 2003/0066800 | A1 |   | 4/2003  | Saim et al. |
| 2003/0072677 | A1 |   | 4/2003  | Kafesjian et al. |
| 2004/0020518 | A1 | * | 2/2004  | DeYoung et al. ............ 134/30 |
| 2004/0023453 | A1 |   | 2/2004  | Xu et al. |
| 2004/0064964 | A1 |   | 4/2004  | Lee |
| 2004/0118281 | A1 | * | 6/2004  | Leitch et al. ................ 95/236 |
| 2005/0229323 | A1 | * | 10/2005 | Mills et al. ................ 8/94.11 |
| 2007/0003432 | A1 |   | 1/2007  | Christensen et al. |
| 2007/0173403 | A1 |   | 7/2007  | Koike et al. |

OTHER PUBLICATIONS

White et al Journal of Biotechnology 123 (2006) 504-515.*
Office Action from the United States Patent and Trademark Office, U.S. Appl. No. 12/151,840, filed May 8, 2008, First Named Inventor: Maximilian A. Biberger, Mail Date: Nov. 25, 2009.
United States Patent and Trademark Office, Advisory Action, Mailed: May 27, 2010, U.S. Appl. No. 12/151,840, filed May 8, 2008, First Named Inventor: Maximilian A. Biberger, 3 pages.
United States Patent and Trademark Office, Office Action, Mailed: Mar. 18, 2010, U.S. Appl. No. 12/151,840, filed May 8, 2008, First Named Inventor: Maximilian A. Biberger, 20 pages.
United States Patent and Trademark Office Action mailed Jul. 21, 2010, for U.S. Appl. No. 12/151,840, filed May 8, 2008, pp. 1-24.
Office Action dated Jun. 24, 2009, U.S. Appl. No. 12/151,840, filed May 8, 2008.
Non-Final office action dated Sep. 28, 2011, U.S. Appl. No. 12/151,841, filed May 8, 2008.
White, A. et al. (2006). "Effective Terminal Sterilization Using Supercritical Carbon Dioxide," *Journal of Biotechnology* 123: 504-515.
U.S. Appl. No. 12/151,841, filed May 8, 2008, for Biberger.
Notice of Allowance mailed Apr. 25, 2011, including an Examiner-initiated Interview Summary for U.S. Appl. No. 12/151,840, filed May 8, 2008, for Biberger et al., 13 pages.
Advisory Action mailed on Mar. 8, 2011, for U.S. Appl. No. 12/151,840, filed May 8, 2008, for Biberger et al., 3 pages.
Final Office Action mailed on Jan. 4, 2011, for U.S. Appl. No. 12/151,840, filed May 8, 2008, for Biberger et al., 24 pages.
Advisory Action mailed on Feb. 4, 2010, for U.S. Appl. No. 12/151,840, filed May 8, 2008, for Biberger et al., 3 pages.
Final Office Action mailed on Feb. 3, 2012, for U.S. Appl. No. 12/151,841, filed May 8, 2008, for Biberger, 18 pages.

* cited by examiner

*Primary Examiner* — Anoop Singh
(74) *Attorney, Agent, or Firm* — Morrison & Foerster LLP

(57) ABSTRACT

A method of processing soft tissue and skin using supercritical fluids is disclosed. The method comprises placing the soft tissue or skin on a scaffold in a processing chamber, adding supercritical fluid to the processing chamber, and pulsing the supercritical fluid in the processing chamber. A processing system for processing soft tissue and skin using supercritical fluids in accordance with the present invention comprises a processing chamber for housing the soft tissue, a scaffold, a vat for storing a processing fluid, a pump, a heating element, and a flow path.

16 Claims, 5 Drawing Sheets

SYSTEM FOR AND METHOD OF PROCESSING SOFT TISSUE AND SKIN WITH FLUIDS USING TEMPERATURE AND PRESSURE CHANGES

RELATED APPLICATIONS

This Patent Application is with U.S. patent application Ser. No. 12/151,840, filed May 8, 2008, and entitled "SYSTEM AND METHOD OF PROCESSING BONE MATERIAL USING SUPERCRITICAL FLUIDS", now U.S. Pat. No. 8,007,718, hereby incorporated by reference, and claims priority under 35 U.S.C. 119 (e) of the U.S. Provisional Patent Application Ser. No. 60/928,946, filed May 11, 2007 and entitled "MATERIAL PRODUCTION SYSTEM AND METHOD", which is hereby incorporated by reference.

FIELD OF THE INVENTION

The present invention relates generally to the field of processing soft tissue and skin. More specifically, the present invention relates to a system for and a method of processing soft tissue and skin with fluids using temperature and pressure changes.

BACKGROUND

Soft tissue and skin (hereinafter collectively "soft tissue" or "tissue") are in high demand for grafting purposes. Unfortunately, soft tissue is difficult to process and sterilize properly using conventional methods for several reasons.

First, conventional soft tissue processing methods are complex, expensive, labor-intensive, and time-consuming, because the methods typically require the gradual application of a multitude of chemicals and reagents in a number of processing chambers.

Second, some conventional methods stress and distort the tissue, such that the tissue no longer retains its desired biological and biochemical properties, by virtue of the multiple applications of chemicals and reagents, as well as the repeated handling and transferring of the tissue from one processing chamber to the next. Such stress and distortion of the tissue can make the tissue unmanageable and unacceptable for graft purposes.

Third, even with the gradual application of chemicals and reagents, some conventional methods do not penetrate the tissue enough to destroy, lyse, or eliminate contaminants, such as donor cells, donor blood, viruses, bacteria, spores, fungi, and the like. If the tissue is not successfully penetrated and processed to eliminate such contaminants, this can result in dangerous transfers of unwanted, sometimes fatal, viral, bacterial, and infectious diseases, such as HIV and hepatitis, from the donor to the host. Also, if the donor's cells and blood inadvertently remain on the tissue, then upon implantation of the tissue into the host, the host's body will likely mount an immunogenic response to the contaminated tissue and may reject the tissue.

BRIEF SUMMARY OF THE DISCLOSURE

In accordance with the present invention, a method of processing soft tissue and skin with fluids using temperature and pressure changes comprises three steps. In the first step, the tissue is placed on a scaffold in a processing chamber. In the second step, a fluid is added to the processing chamber. In the third step, the fluid is pulsed in the processing chamber.

It will be apparent to one skilled in the art that the term "pulsing," as set forth in the present invention, refers to the fluctuation of the temperature, the pressure, or a combination of the temperature and the pressure of a fluid, such as $CO_2$, in order to disrupt, lyse, implode, explode and/or crack the walls of contaminants present within the tissue. In some embodiments of the present invention, a supercritical fluid is utilized to treat the tissue. In some embodiments a cryogenic fluid is utilized to treat the tissue. In some embodiments, a fluid is fluctuated between cryogenic and supercritical states to treat the tissue. This can be done any number of ways. Preferably, it can be done by fluctuating the pressure of the supercritical fluid. Alternatively, pulsing can be accomplished by fluctuating the temperature of the supercritical fluid, or by fluctuating both the temperature and the pressure of the supercritical fluid. Alternatively, pulsing can occur from a first supercritical pressure and a second supercritical pressure.

All these steps are performed in situ in the processing chamber. The steps can be performed automatically, thus, dramatically reducing labor costs. The resulting sterilized soft tissue retains its biomechanical and biological properties, making it an ideal tissue graft for implantation.

The present invention also includes a processing system for processing soft tissue with fluid using temperature and pressure changes. The processing system comprises a processing chamber, a scaffold coupled to the processing chamber, a vat, a pump, a heating element, and a flow path. The processing chamber houses the soft tissue to be processed. The scaffold is coupled to the processing chamber and supports the soft tissue, such that the soft tissue retains its structural integrity throughout the operation of the processing system. The vat is coupled to the processing chamber through a flow path. In operation of the system, a processing fluid flows through the flow path from the vat to the processing chamber. According to the preferred embodiment, once the processing fluid successfully enters the processing chamber, the processing fluid undergoes pressure pulsing and temperature pulsing with the help of the pump and the heating element, respectively. In some embodiments of the present invention, a supercritical fluid is delivered to the processing chamber to treat the tissue. In some embodiments a cryogenic fluid is delivered to the processing chamber to treat the tissue. In some embodiments, a fluid is fluctuated between cryogenic and supercritical states to treat the tissue. In yet other embodiments, the processing fluid fluctuates from its supercritical and nonsupercritical states to treat the tissue.

DETAILED DESCRIPTION OF THE DISCLOSURE

Figure 1A:
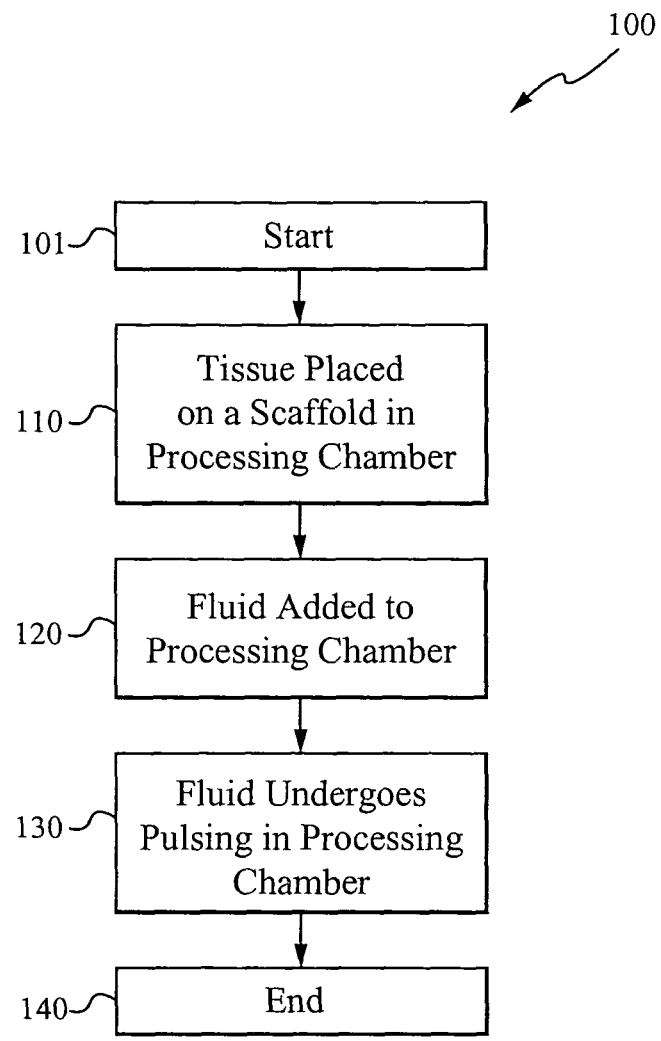
FIG. 1A is a flow chart illustrating a processing sequence of steps for processing soft tissue in accordance with a preferred embodiment of the present invention.

The present invention discloses a method of and a system for processing soft tissue and skin (hereinafter collectively referred to as "tissue" or "soft tissue") with fluids using temperature and/or pressure pulsing. In a preferred embodiment supercritical fluids, such as supercritical $CO_2$ are used to treat the tissue. Supercritical fluids have surprisingly efficient extraction, deep penetration, and cleaning capabilities, particularly with soft tissue. Supercritical fluids are superior to most chemicals and reagents used in the conventional soft tissue processing methods, because supercritical fluids can deeply penetrate and infuse soft tissue like a gas and dissolve undesirable substances, such as fat, bacteria, and viruses, like a liquid. Furthermore, supercritical fluid extraction and processing can be controlled by adjusting certain variables, such as pressure and temperature, so that selected contaminants can be extracted, thereby resulting in sterilized soft tissue and skin that retain their desired biological and biomechanical properties and characteristics.

FIG. 1 illustrates a processing sequence 100 for processing soft tissue in accordance with the preferred embodiment of the invention. At the start step, the step 101, a soft tissue is harvested from the donor and is ready for processing. In the preferred embodiment, the soft tissue is an allograft, from a human donor or a cadaver, intended for implantation into a human host. However, it will be apparent to those skilled in the art that the present invention can also be used in autografts and xenografts alike. At the step 110, the soft tissue to be processed is placed on a scaffold in a processing chamber. The scaffold is configured to support the soft tissue, such that the soft tissue will not undergo stress or distortion during the processing method. The scaffold can be configured in any number of ways, so long as it supports the soft tissue during the process, such that the soft tissue does not distort, curl, twist, ripple, wrinkle, cracking, or otherwise be physically altered due to lack of support. For instance, the scaffold can be a simple mount upon which to flatly lay the soft tissue, or it can grip the soft tissue such that the tissue remains taut and does not collapse during or after the processing method. At the step 120, fluid is then added to the processing chamber that houses the soft tissue. Preferably, the fluid is supercritical $CO_2$.

Next, at the step 130, the supercritical fluid inside the processing chamber undergoes pulsing to kill and extract contaminants, such as pathogens, donor cells, donor blood, viruses, bacteria, fungi, spores, and the like.

As mentioned above, the term "pulsing," as set forth in the present invention and specifically in the step 130, refers to the fluctuation of the temperature, the pressure, or a combination of the temperature and the pressure of a fluid, such as $CO_2$, in order to disrupt, lyse, implode, explode and/or crack the walls of contaminants present within the tissue. In some embodiments of the present invention, a supercritical fluid is utilized to treat the tissue. In some embodiments a cryogenic fluid is utilized to treat the tissue. In some embodiments, a fluid is fluctuated between cryogenic and supercritical states to treat the tissue. This can be done any number of ways. Preferably, it can be done by fluctuating the pressure of the supercritical fluid. Alternatively, pulsing can be accomplished by fluctuating the temperature of the supercritical fluid, or by fluctuating both the temperature and the pressure of the supercritical fluid. Alternatively, pulsing can occur from a first supercritical pressure and a second supercritical pressure.

In the preferred embodiment, $CO_2$ fluctuates in a cycle from its supercritical state to its nonsupercritical state, through the varying ranges of pressure and temperature. It is well known that $CO_2$ reaches its supercritical state when the temperature is above 30.5 degrees Centigrade and the pressure is above 1070.4 psi. As a result of the pressure pulsing and temperature pulsing of the supercritical fluid, at the step 130, the supercritical fluid can explode and implode the undesirable contaminants. The supercritical fluid infuses into the undesirable contaminants within the soft tissue and destroys the contaminants through the pulsing step. In the preferred embodiment, the pulsing step is rapid, which in turn causes the supercritical fluid to disrupt, lyse and crack the walls of the contaminants.

A benefit of using supercritical fluid lies in the ability of supercritical fluid to destroy prions. Prions are misshapen proteins typically found in fat that are thought to be linked with neurodegenerative diseases, such as mad cow disease, fatal familial insomnia, Gerstmann-Straussler syndrome, and Creutzfeldt-Jakob disease, to name a few. Prions are extremely difficult to kill, and under some conventional methods, strong oxidizers are used to accomplish this task. However, strong oxidizers in the conventional method can be advantageously replaced by supercritical fluids in the present invention, since supercritical fluids also eliminate prions. Thus, the use of supercritical fluid as an extractor of contaminants, including prions, during the pulsing step at the step 130 (FIG. 1) in accordance with the present invention, prevents the transfer of diseases from the donor to the host via a tissue transplant, without the disadvantage of using a multitude of strong, sometimes toxic, chemicals and reagents.

Optionally, within the step 130, contaminants are flushed using a recirculation loop system in which the contaminants and the supercritical fluid exit the processing chamber. The contaminants are filtered out from the supercritical fluid using a filter, and the remaining supercritical fluid reenters the processing chamber through a loop, for the supercritical fluid to be reused for the next cycle.

In an alternative embodiment, the supercritical fluid enters the processing chamber through a flow path. Through pulsing, the supercritical fluid extracts the contaminants, which separate from soft tissue without a filter or a recirculation loop. For instance, contaminants can separate from soft tissue through condensation, preferably in one processing chamber. Those skilled in the art will also recognize other processes for separating contaminants from soft tissue, without using filtration or recirculation systems. Finally, at the step 140, the processing of the soft tissue is completed.

One advantage of the present invention is that the final product is the ideal soft tissue material; that is, it retains its biomechanical and biological properties and is also clean of contaminants, such as viruses, bacteria, donor cells, donor blood, spores, fungi, pathogens, prions, fats, and the like. Another distinct advantage is that the processed soft tissue is deeply penetrated by the supercritical fluid for a cleaner sterilization, and yet it does not undergo unnecessary stress or distortion, since the scaffold supports the soft tissue throughout the process. A further advantage lies in the fact that the entire processing method can be accomplished within one single chamber, and thus requires little, if any, handling or transferring of the soft tissue.

In the preferred embodiment of the present invention, all these steps are performed in situ in the processing chamber. The steps can be performed automatically, thus, dramatically reducing labor costs.

Figure 1B:
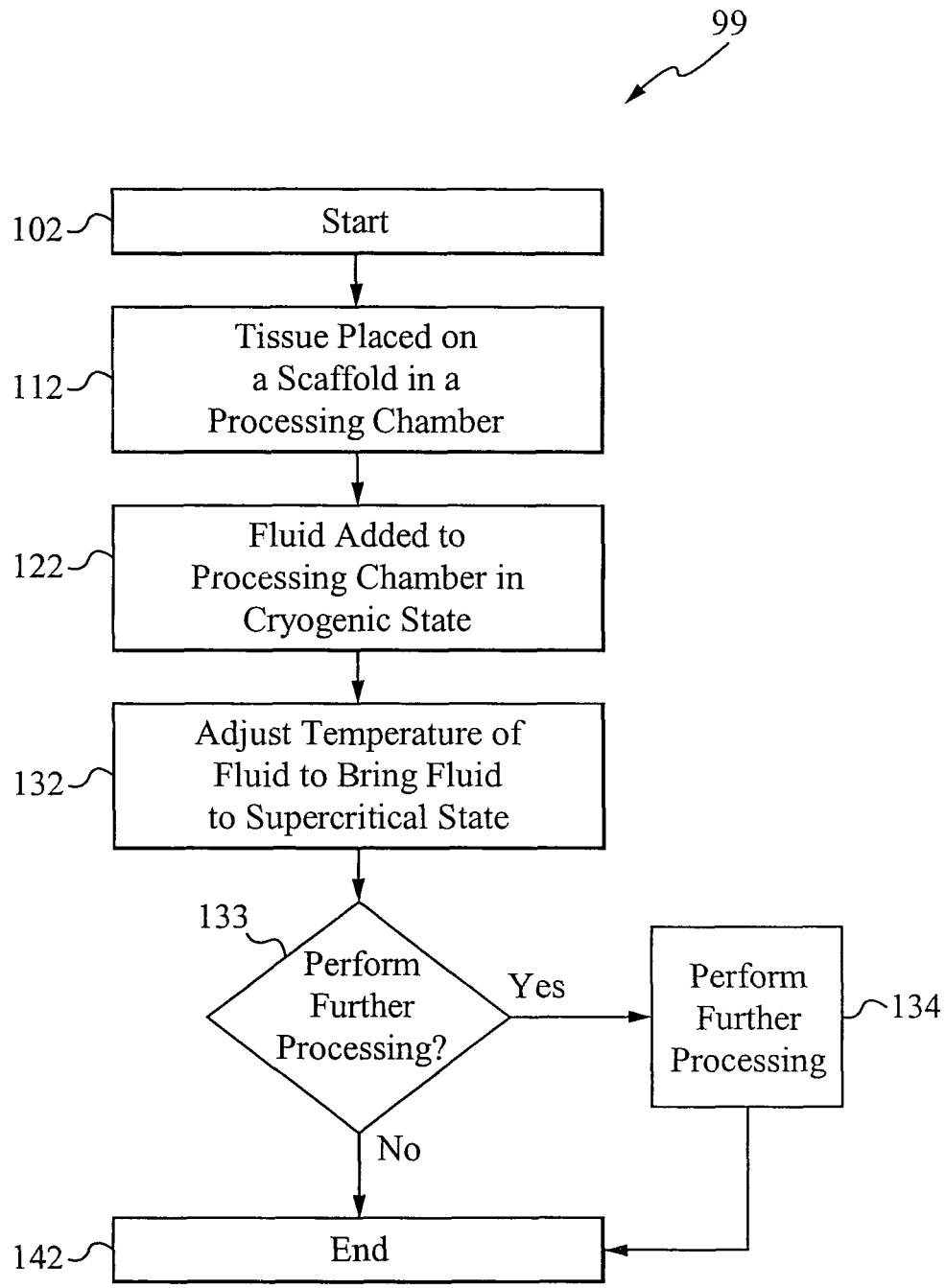
FIG. 1B is a flow chart illustrating a processing sequence of steps for processing soft tissue in accordance with some embodiments of the present invention.

FIG. 1B illustrates an alternative processing sequence 99 for processing soft tissue in accordance with alternate embodiments of the invention. The process depicted in FIG. 1B takes advantage of the events from temperature change on cellular bodies. Specifically, the process introduces very cold fluid to a processing chamber and heats the liquid to a supercritical state, thus causing the fluid to rupture cell structure.

At the start step, the step 102, a soft tissue is harvested from the donor and is ready for processing, as explained above. At the step 112, the soft tissue to be processed is placed on a scaffold in a processing chamber, as explained above. At the step 122, fluid is added to the processing chamber in a cryogenic state. For the purpose of this disclosure the term "cryogenic" shall be interpreted as a fluid in a cold state with temperatures well below 0° C. In the preferred embodiment of the present invention, the cryogenic fluid comprises liquid $CO_2$ at a temperature near −30° C.

Then, at step 132 the temperature of the fluid is increased. In some embodiments of the present invention, the temperature change is effectuated using a heater coupled with the processing chamber. In the preferred embodiment, cryogenic $CO_2$ is heated to a supercritical state. According to this embodiment, the heating of cryogenic $CO_2$ to the supercritical state causes the $CO_2$ to rupture cellular structures.

At step 133 a determination is made whether to conduct further processing of the organic material. For example, degreasing steps, further pulsing steps, infusion steps, drying steps, etc may be utilized. If an operator chooses to conduct further processing, the processing occurs at step 134. The process sequence ends at step 142, when the material is removed from the processing chamber.

Figure 1C:
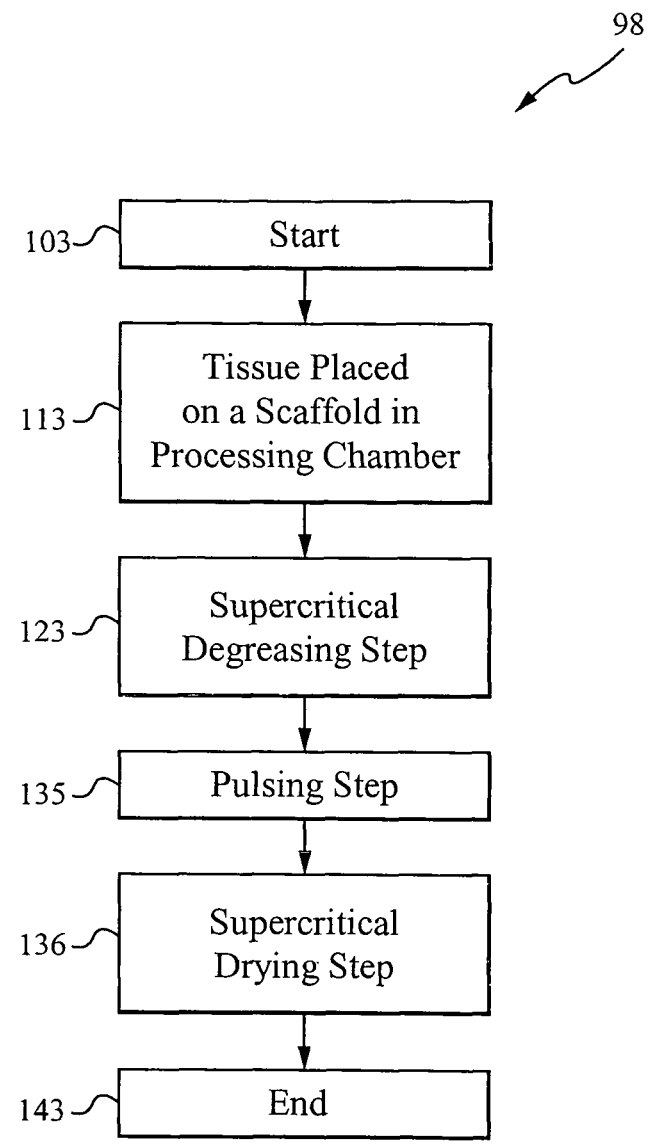
FIG. 1C is a flow chart illustrating a processing sequence of steps for processing soft tissue in accordance with some embodiments of the present invention.

FIG. 1C illustrates yet another alternative processing sequence 98 for processing soft tissue in accordance with alternate embodiments of the invention. At the start step, the step 103, a soft tissue is harvested from the donor and is ready for processing, as explained above. At the step 113, the soft tissue to be processed is placed on a scaffold in a processing chamber, as explained above.

Next, at the step 123, a supercritical degreasing step is performed. The supercritical degreasing step 123 involves delivering a supercritical fluid mixed with a degreasing chemistry to the processing chamber that holds the soft tissue material. The degreasing chemistry aides in soft tissue degreasing and in extracting liquids from the soft tissue matrix. Preferably, the supercritical fluid is supercritical CO2 and the degreasing chemistry is an alcohol, such as acetone. It is well known that CO2 reaches its supercritical state when the temperature is above 30.5 degrees Centigrade and the pressure is above 1070.4 psi. The degreasing step 123 concludes with flushing the supercritical fluid and degreasing chemistry from the processing chamber.

Next, a pulsing step 135 is performed as described above. The pulsing step 135 ends with flushing the fluid and the contaminants from the processing chamber. In some embodiments of the present invention a recirculation loop system is utilized to reuse supercritical fluid after the contaminants and the supercritical fluid exit the processing chamber. In some embodiments of the present invention, the contaminants are filtered out from the supercritical fluid using a filter, and the remaining supercritical fluid reenters the processing chamber through a loop, for the supercritical fluid to be reused for another next cycle.

In an alternative embodiment, the supercritical fluid enters the processing chamber through a flow path. Through pulsing, the supercritical fluid extracts the contaminants, which separate from biological material without a filter or a recirculation loop. For instance, contaminants can separate from biological material through condensation, preferably in one processing chamber. Those skilled in the art will also recognize other processes for separating contaminants from soft tissue material, without using filtration or recirculation systems.

Next, at the step 136, the soft tissue material is dried using supercritical fluid and a drying chemistry. In some embodiments of the present invention, a combination of supercritical CO2 and alcohol is used for the proper rinsing of the soft tissue material. In some embodiments of the present invention, acetone is used as the drying chemistry. The use of the supercritical drying step presents clear advantages over the prior art because using supercritical fluid for the delivery of the drying chemistry allows the drying agent to more-fully permeate the soft tissue matrix to remove unwanted moisture. This step of drying is important due to the adverse effects of left over moisture with the soft tissue matrix such as the prevention of cell migration through the structure and the cracking of the soft tissue structure as the biological material is cooled down to preserve the graft, among other negative effects. Finally, at the step 143, the biological material is ready to be implanted into the host's body.

The processes illustrated in FIGS. 1A through 1C depict three alternative embodiments of processing soft tissue. However, it will be clear to those having ordinary skill in the art that any number of processing techniques or sequences may benefit from pulsing performing pulsing.

In the preferred embodiment of the present invention, the processing steps discussed above (in FIGS. 1A-1C) are performed in-situ within a single processing chamber, thus reducing the amount of manual labor associated with processing. However, it will be readily apparent to those having ordinary skill in the relevant art that processing may be performed in any number of processing chambers, whilst utilizing the novel features of the present invention.

Figure 2A:
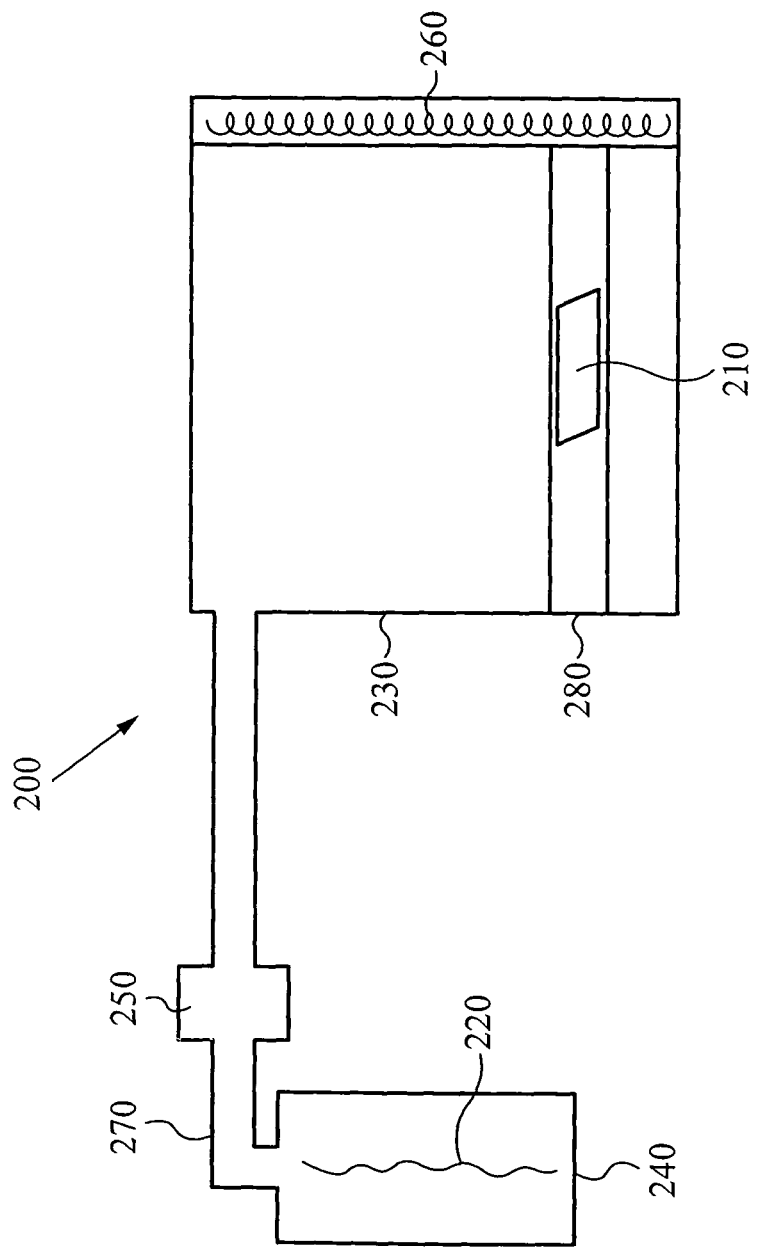
FIG. 2A is a block diagram illustrating a processing system for processing soft tissue in accordance with the preferred embodiment of the present invention.

A processing system for processing fluid is also disclosed. FIG. 2A illustrates a processing system 200 for processing soft tissue 210 using a processing fluid 220, in accordance with the preferred embodiment. In some embodiments, the processing fluid 220 is supercritical $CO_2$. In other embodiments, the processing fluid is cryogenic $CO_2$. However, it will be readily apparent to those having ordinary skill in the relevant art that a wide range of processing chemistries having a range of temperatures and pressures are suitable for use. The processing system 200 comprises a processing chamber 230, a vat 240, a pump 250, a heating element 260, a flow path 270, and a scaffold 280. The scaffold 280 is coupled to the processing chamber 230 and preferably, the scaffold is inside the processing chamber 230. The scaffold 280 is configured to support the soft tissue 210, such that the soft tissue 210 does not undergo stress or distortion during the processing method. The scaffold 280 can be configured in any number of ways, so long as it supports the soft tissue 210 and prevents distortion or stress. Distortion and stress includes, but is not limited to, curling, collapsing, twisting, wrinkling, rippling, cracking, or any other physical or material alteration due to lack of support. For instance, the scaffold 280 can be configured to grip or hold the soft tissue 210 taut. In another embodiment, the scaffold 280 can be a type of flat mount that allows for the soft tissue 210 to lay flat within the processing chamber 230. Those skilled in the art will recognize that the actual configuration and elements of the scaffold 280 is largely dependent upon the type and dimensions of the soft tissue 210 being processed.

The processing chamber 230 is coupled to the vat 240 through the flow path 270. The pump 250 and the heating element 260 are coupled to the processing chamber 230. Preferably, the pump 250 is coupled to the flow path 270, which eventually leads to the processing chamber 230. Preferably, the heating element 260 is outside the processing chamber 230.

Initially, the processing chamber 230 houses the soft tissue 210 to be processed. In the preferred embodiment, the soft tissue 210 is an allograft from a human donor intended for a human host. While FIG. 2A illustrates a processing system 200 having a single processing chamber 230, it will be apparent to those skilled in the art that the processing system 200 can comprise any number of processing chambers for performing multiple processes on soft tissue or for concurrently processing multiple soft tissues.

The processing fluid 220 initially is inside the vat 240. The vat 240 is coupled to the processing chamber 230 through a flow path 270. In operation, once the processing of the soft tissue 210 begins, the supercritical fluid 220 flows from the vat 240 through the flow path 270 and into the processing chamber 230. Once the processing fluid 220 successfully enters the processing chamber 230, the processing fluid 220 undergoes pulsing to begin the extraction of the contaminants contained on or within the soft tissue 210.

The term "pulsing" in reference to the processing system 200 refers to the fluctuation of the processing fluid 220, such as $CO_2$, between its nonsupercritical state and its supercritical state or from one supercritical pressure and another supercritical pressure. As a result of pulsing the processing fluid 220, undesirable contaminants are extracted. Pulsing can be done any number of ways. Preferably, pulsing can be accomplished by fluctuating the pressure of the processing fluid 220 with the help of the pump 250. Alternatively, temperature pulsing can be applied to the processing fluid 220 with the heating element 260. In yet another alternative embodiment, both pressure pulsing and temperature pulsing can be accomplished with the help of the pump 250 and the heating element 260, respectively. Alternatively, pulsing can occur from a first supercritical pressure and a second supercritical pressure.

It will be apparent to those skilled in the art how the supercritical fluid 220 can be cooled at times to reach its nonsupercritical state. For instance, the processing chamber 230 can be opened at certain times, or a refrigerant agent can be added to the processing system 200, to lower the temperature of the processing fluid 220.

In the preferred embodiment, the processing fluid 220 infuses into the undesirable contaminants and, if necessary, lyses those contaminants. Such contaminants include but are not limited to viruses, bacteria, donor cells, fungi, spores, donor blood, and the like. Finally, the processing of the soft tissue 210 is completed. After its processing through the processing system, the final product is a sterile, contaminant-free soft tissue that retains its biomechanical and biological properties, making it an ideal soft tissue for implantation. Such an ideal soft tissue translates to a shorter healing time for the host, an easier incorporation of the tissue by the host, higher biocompatibility with the host, fewer post-implant operations, shorter hospital stays, and less expense for the host.

It will be readily apparent to one skilled in the art that various modifications may be made to the embodiments without departing from the spirit and scope of the invention. For instance, a recirculation loop, additional chemistry vats, or the like can be optionally added to the processing system.

Figure 2B:
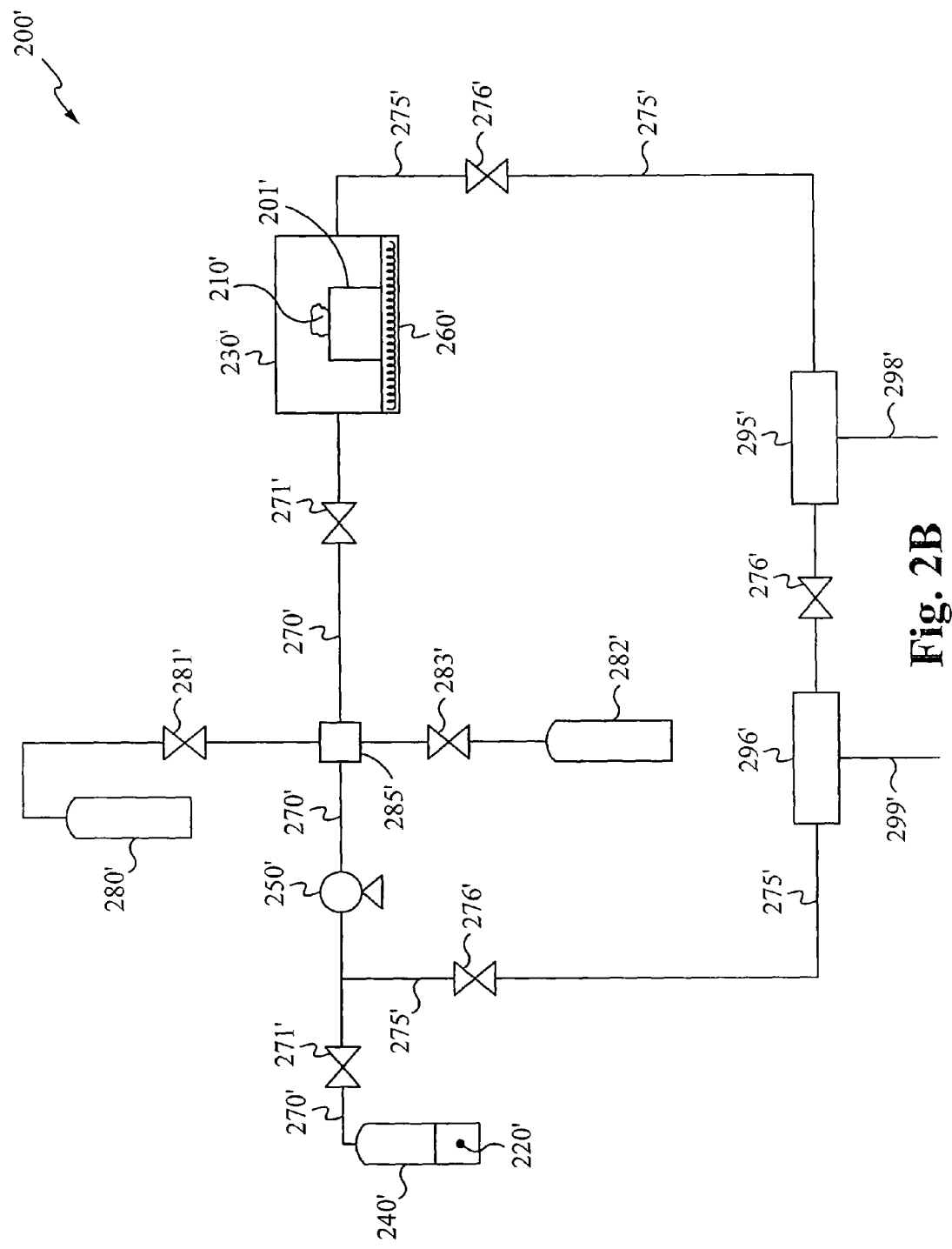
FIG. 2B is a block diagram illustrating a processing system for processing soft tissue in accordance with the some embodiments of the present invention.

FIG. 2B illustrates a processing system 200' for processing soft tissue material 210' using a processing fluid 220' in accordance with some embodiments of the present invention. The processing system 200' comprises a processing chamber 230', a vat 240', a pump 250', a flow path 270', a valve 271', a first chemistry tank 280', a second chemistry tank 282', a mixer 285', a recirculation loop 275', and components 295' and 296'. The processing chamber 230' contains a scaffold 201' and the soft tissue 210'.

As shown in FIG. 2B, the vat 240', the first chemistry tank 280' and the second chemistry tank 282' are coupled to the mixer 285'. A valve 281' is provided between the first chemistry tank 280' and the mixer 285' to optionally ensure that fluid delivered to the mixer 285' from the first chemistry tank 280' possesses some prerequisite pressure. Likewise, a valve 283' is provided between the second chemistry tank 282' and the mixer 285'. In some embodiments of the present invention, heaters (not shown) heat the chemistry contained within the chemistry tanks to heat the chemistries to some prerequisite temperature.

The mixer 285' is configured to receive and mix processing fluid 220' from the vat 240' and one or more chemistries from the first chemistry tank 280' and/or the second chemistry tank 282'. The mixed fluid is delivered via the flow path 270' to the processing chamber 230'. A valve 231' is positioned between the mixer 285' and the processing chamber 230' to optionally ensure that fluid delivered from the mixer 285' to the processing chamber 230' possesses some prerequisite pressure. In some embodiments of the present invention, the valve 231' is dynamically controllable to vary the pressure of the fluid delivered to the processing chamber in order to accomplish the pulsing step, as explained above. Likewise, a heating element 260' is coupled to the processing chamber 230' and the heating element 260' is dynamically controllable to vary the temperature of the fluid delivered to the processing chamber in order to accomplish the pulsing step, as explained above.

According to FIG. 2B, the fluid in the processing chamber 230' exits the processing chamber 230' into a recirculation loop 275'. A number of valves 276' are positioned within the recirculation loop 275' to control pressure. Also contained within the recirculation loop 275' are components 295' and 296'. Components 295' and 296' can include, but are not limited to separator, filters or the like. In some embodiments of the present invention, outlet lines 298' and 299' are coupled to the components 295' and 296', respectively.

In some embodiments of the present invention, contaminants are filtered out from the processing fluid, leaving remaining fluid. The recirculation loop 275' is configured such that the remaining fluid reenters the flow path 270' to be reused for the next processing cycle. Any number of cycles and types of filters necessary to extract undesirable contaminants of soft tissue material can be used, based on the application at hand.

Reference has been made in detail to the preferred and alternative embodiments of the invention, examples of which are illustrated in the accompanying drawings. While the invention has been described in conjunction with the preferred embodiments, it will be understood that they are not intended to limit the invention to these embodiments. On the contrary, the invention is intended to cover alternatives, modifications and equivalents, which may be included within the spirit and scope of the invention. Furthermore, in the detailed description of the present invention, numerous specific details have been set forth in order to provide a thorough understanding of the present invention. However, it should be noted that the present invention may be practiced without these specific details. In other instances, well known methods, procedures and components have not been described in detail as not to unnecessarily obscure aspects of the present invention.

What is claimed is:

1. A method of processing soft tissue comprising:
   a) providing soft tissue, wherein the soft tissue contains contaminants;
   b) coupling the soft tissue to a scaffold positioned within a processing chamber;
   c) introducing only supercritical $CO_2$ and a degreasing agent into the processing chamber, wherein the degreasing agent is an alcohol or acetone; and d) performing a pulsing step on the supercritical $CO_2$ and degreasing agent, wherein the pulsing step comprises fluctuating pressure of the supercritical $CO_2$ and degreasing agent, wherein the supercritical $CO_2$ and degreasing agent fluctuates between its supercritical and nonsupercritical states, and wherein the pulsing step kills substantially all the contaminants present within the soft tissue.

2. The method of claim 1, wherein the pulsing step agitates the contaminants present in the soft tissue, thereby removing the contaminants from the soft tissue.

3. The method of claim 1, wherein the degreasing agent is acetone.

4. The method of claim 1, further comprising:
introducing a drying chemistry into the processing chamber after the pulsing step, wherein the drying chemistry comprises a supercritical fluid and a drying agent.

5. The method of claim 4, wherein the drying agent is acetone.

6. The method of claim 1, further comprising:
exposing the soft tissue to gamma-ray radiation.

7. The method of claim 1, further comprising:
a) removing the fluid from the processing chamber into a recirculation loop;
b) filtering the fluid in the recirculation loop, forming a filtered fluid; and
c) re-introducing the filtered fluid into the processing chamber.

8. The method of claim 1, further comprising:
a) introducing at least one additional portion of fluid into the processing chamber;
b) performing at least one additional pulsing step on the at least one additional portion of fluid.

9. A method of processing soft tissue comprising:
a) providing soft tissue, wherein the soft tissue contains contaminants;
b) coupling the soft tissue to a scaffold positioned within a processing chamber;
c) introducing cryogenic $CO_2$ into the processing chamber;
d) performing a pulsing step on the cryogenic $CO_2$, wherein the pulsing step comprises heating the cryogenic $CO_2$ to a supercritical state, forming supercritical $CO_2$, wherein the supercritical $CO_2$ fluctuates between its cryogenic and supercritical states, and wherein the pulsing step kills substantially all the contaminants present within the soft tissue.

10. A method of processing soft tissue comprising:
a) providing soft tissue, wherein the soft tissue contains contaminants;
b) coupling the soft tissue to a scaffold positioned within a processing chamber;
c) introducing supercritical $CO_2$ into the processing chamber; and
d) performing a pulsing step on the supercritical $CO_2$, wherein the pulsing step comprises fluctuating pressure of the supercritical $CO_2$, wherein the supercritical CO2 fluctuates between its supercritical and nonsupercritical states, and wherein the pulsing step kills substantially all the contaminants present within the soft tissue.

11. The method of claim 9, further comprising:
introducing a drying chemistry into the processing chamber after the pulsing step, wherein the drying chemistry comprises a supercritical fluid and a drying agent.

12. The method of claim 11, wherein the drying agent is acetone.

13. The method of claim 9, further comprising:
exposing the soft tissue to gamma-ray radiation.

14. The method of claim 10, further comprising:
introducing a drying chemistry into the processing chamber after the pulsing step, wherein the drying chemistry comprises a supercritical fluid and a drying agent.

15. The method of claim 14, wherein the drying agent is acetone.

16. The method of claim 10, further comprising:
exposing the soft tissue to gamma-ray radiation.

\* \* \* \* \*